United States Patent [19]
Argoudelis et al.

[11] Patent Number: 5,616,320
[45] Date of Patent: Apr. 1, 1997

[54] USE OF ANTIBIOTICS 10381B TO PROMOTE GROWTH

[75] Inventors: Alexander D. Argoudelis, deceased, late of Portage, by Cassandra Argoudelis, legal representative; Franklin B. Shilliday, Kalamazoo; Alice L. Laborde, Augusta; Scott E. Truesdell, Portage; Oldrich K. Sebek, Kalamazoo, all of Mich.

[73] Assignee: The Upjohn Company, Kalamazoo, Mich.

[21] Appl. No.: 312,016

[22] Filed: Sep. 26, 1994

Related U.S. Application Data

[63] Continuation of Ser. No. 214,089, Mar. 16, 1994, abandoned, which is a continuation of Ser. No. 861,337, Mar. 30, 1992, abandoned, which is a continuation of Ser. No. 346,900, Feb. 27, 1989, abandoned, which is a continuation-in-part of Ser. No. 35,678, Dec. 3, 1986, abandoned, Ser. No. 882,075, Jul. 3, 1986, abandoned, Ser. No. 718,919, Apr. 2, 1985, abandoned, PCT/US87/01450, Jun. 25, 1987, abandoned, and PCT/US86/00657, May 31, 1986, abandoned.

[51] Int. Cl.⁶ .................................................. A61K 35/00
[52] U.S. Cl. .............................. 424/71.3; 426/2; 426/71; 514/2
[58] Field of Search .............................. 426/2, 71; 514/2; 424/115

[56] References Cited

U.S. PATENT DOCUMENTS

| 4,007,090 | 2/1977 | Chaiet | 195/80 R |
| 4,061,372 | 12/1977 | Muir et al. | 424/117 |
| 4,061,732 | 12/1977 | Muir | 424/117 |
| 4,243,661 | 1/1981 | Ishihara | 424/117 |

FOREIGN PATENT DOCUMENTS

| 17599 | 7/1968 | Japan . |
| 45-6880 | 3/1970 | Japan . |
| WO86/05785 | 10/1986 | WIPO . |
| WO88/00200 | 1/1988 | WIPO . |

OTHER PUBLICATIONS

"Bergey's Manual of Determinative Bacteriology", Buchanan et al., ed 1974, Williams & Wilkins, p. 503.
Muir et al., *J. Anim. Sci.*, 48(3), pp. 468–473 1979.
Bergey's Manual of Systematic Bacteriology, vol. 2, p. 1069, 1986, Sneath et al. ed., Williams & Wilkins.
Argoudelis, A.D., et al., The Journal of Antibiotics, XL (6):750–760, Jun. 1987.
Egawa, Y., et al., J. Antibiotics, 22:12–17 (1969).
Fox, J.J., et al., Tetrahedron Letters, 57:6029–6032 (1968).
Haskell, T.H., et al., J. Amer. Chem. Soc., 80:743–747 (1958).
Seto, H., and Yonehara, H., The J. of Antibiotics, XXX (11):1022–1024, Nov. 1977.
Stevens, C.L., et al., J. Org. Chem., 31:2822–2828 (1966).
Yonehara, H., and Otake, N., Tetrahedron Letters, 32:3785–3791 (1966).
Bunyan, J., et al., Br. Poult. Sci., *Antimicrobial Substances and Chick Growth Promotion: The Growth-Promoting Activities of Antimicrobial Substances, Including Fifty-Two used Either in Therapy or as Dietary Additives*, 18:283–294 (1977).
Burg, R. W., ASM News, *Fermentation Products in Animal Health*, 48(10):460–463 (1982).
Muir, L. A. and Barreto, Jr., A., J. Anim. Sci., *Sensitivity of Streptococcus Bovis to Various Antibiotics*, 48(3):468–473 (1979).
Muir, L. A., J. Anim. Sci., *Mode of Action of Exogenous Substances on Animal Growth—An Overview*, 61(Suppl. 2):154–180 (1985).
Muir, L. A., et al., J. Anim. Sci., *Control of Wheat–Induced Lactic Acidosis in Sheep by Thiopeptin and Related Antibiotics*, 50(3):547–553 (1980).

Primary Examiner—Irene Marx
Attorney, Agent, or Firm—Martha A. Gammill

[57] ABSTRACT

Antibiotic $10381a_1$, wherein R is hydrogen, is a cytosine-containing antibiotic producible by culturing the novel microorganism *Streptomyces arginensis* in an aqueous medium and isolation thereof. Derivatives wherein R is a $C_1$ to $C_3$ alkyl ester of antibiotic $10381a_1$, are also disclosed along with the pharmaceutically acceptable salts of both the native and esterified forms. Antibiotic $10381a_1$ inhibits the growth of selected species of yeast, fungi and bacteria. This invention also relates to a novel process for the preparation of the antibiotics 10381b and to a method of using antibiotics 10381b to promote growth in meat-producing animals. These antibiotics are also obtained by the fermentation of a nutrient medium with the novel microorganism *Streptomyces arginensis* and are active against selected species of bacteria.

2 Claims, No Drawings

USE OF ANTIBIOTICS 10381B TO PROMOTE GROWTH

CROSS-REFERENCE TO RELATED APPLICATIONS

This application is a continuation of U.S. application, Ser. No. 08/214,089, filed 16 Mar. 1994, now abandoned, which is a continuation of U.S. application, Ser. No. 07/861,337, filed 30 Mar. 1992, now abandoned, which is a continuation of U.S. application, Ser. No. 07/346,900, filed 27 Feb. 1989, now abandoned, which is a continuation-in-part of the following applications: International application PCT/US87/01450, filed 25 Jun. 1987, which designated the U.S., (now abandoned); U.S. application, Ser. No. 07/035,678, filed 3 Dec. 1986, now abandoned; International application PCT/US86/00657, filed 31 Mar. 1986, which designated the U.S., (now abandoned); U.S. application, Ser. No. 06/882,075, filed 3 Jul. 1986 (now abandoned); and U.S. application, Ser. No. 06/718,919, filed 2 Apr. 1985 (now abandoned).

BACKGROUND OF THE INVENTION

1. Field of the Invention

This invention concerns cytosine-containing antibiotic $10381a_1$ and antibiotics 10381b, which are obtained by the fermentation of a nutrient medium with a new species of Streptomyces, *Streptomyces arginensis*. Antibiotics 10381b comprise a group of at least five antibacterial agents active mainly against G-positive organisms and having physical properties similar to those reported for the sulfomycin group of antibiotics.

2. Information Disclosure

Cytosine-containing antibiotics are known in the art. The nucleoside antibiotic gougerotin is disclosed in J. J. Fox et al., Tetrahedron Letters, No. 57, pp. 6029–6032 (1968). The antibiotics amicetin, plicacetin and bamicetin are disclosed in T. H. Haskell et al., J. Amer. Chem. Soc., 80:743–747 (1958). The antibiotics amicetin and bamicetin are also disclosed in C. L. Stevens et al., J. Org. Chem., 31:2822–2828 (1966). The antibiotic blasticidin S is disclosed in H. Yonehara and N. Otake, Tetrahedron Letters, 32:3785–3791 (1966) and in H. Seto and H. Yonehara, The J. of Antibiotics, XXX (11):1022–1024, November 1977.

None of the prior art antibiotics known to Applicant teaches or suggests antibiotic $10381a_1$. In addition, there are accordingly unexpected and advantageous properties associated with this new antibiotic $10381a_1$, e.g., greatly reduced toxicity.

The production and properties of arginomycin (antibiotic $10381a_1$) are described in International Application, PCT/US86/00657 (International Publication Number WO86/05785 dated 9 Oct. 1986), and in A.D. Argoudelis et al., The Journal of Antibiotics, XL (6):750–760, June 1987.

The production and properties of antibiotics 10381b are described in International Application PCT/US87/01450 (International Publication Number WO 88/00200 dated 14 Jan. 1988.

*Strepomyces arginensis* (Culture 10381) also produces a mixture of solvent-soluble compounds useful as antibiotics against Gram-positive organisms including "resistant" *Staphylococcus aureus*. These antibiotics have been designated as 10381b antibiotics. The present invention describes the production, isolation and physical and biological properties of antibiotics 10381b.

Chemically, antibiotics 10381b appear to be related to the sulfomycins, which are reported to be peptides of unknown structure. See Y. Egawa et al., "Sulfomycins, A Series of New Sulfur-Containing Antibiotics. I: Isolation, Purification and Properties." J. Antibiotics, 22:12–17 (1969).

As part of an effort to elucidate the relationship between antibiotics 10381b and the sulfomycins, the antibiotic production patterns of *S. arginensis* and two sulfomycin-producing cultures were compared under the fermentation conditions developed for production of antibiotics 10381b. The three cultures produce activities which appear virtually identical when analyzed by the methods used for antibiotics 10381b. However, only *S. arginensis* produces antifungal activity (antibiotic $10381a_1$/arginomycin).

Sulfomycins produced by *Streptomyces viridochromogenes* ss *sulfomycini* ATCC 29776; UC 8410 were isolated by procedures used for the isolation of the antibiotic 10381b complex. The obtained material was compared to the antibiotic 10381b complex by infrared spectra (IR), ultraviolet spectra (UV), paper chromatography, thin layer chromatography (tlc), high performance liquid chromatography (HPLC) and antibacterial spectra. It appears that antibiotics 10381b are very similar, if not identical, to the sulfomycins. Antibiotic $10381b_2$, the main antibiotic, is almost identical to the main activity produced by the sulfomycin-producing organisms, and all indications are that it is Sulfomycin I, which is known in the art, as discussed below. However, the producing organisms are definitely different. *S. arginensis* (culture 10381) produces arginomycin, while the two sulfomycin-producing cultures do not produce arginomycin or any other antifungal activity.

U.S. Pat. No. 4,007,090 discloses and claims a novel fermentation process for the preparation of sulfomycin from the microorganism *Streptomyces cineroviridis*.

Sulfomycin I is a known Gram-positive antibiotic described in Japan Pat. No. 45-6880 (Derwent Abstract, Accession Number 18445R). Sulfomycin II and III are also described in the literature as Gram-positive antibiotics in Japan Pat. publication No. 17599/1970 (Derwent Abstract, Accession Number 42550R). All three Sulfomycin antibiotics were prepared by the fermentation of a strain of the microorganism *Streptomyces viridochromogenes*.

SUMMARY OF THE INVENTION

This invention concerns cytosine-containing antibiotics of formula I wherein R is hydrogen or an alkyl of 1 to 3 carbon atoms, inclusive. The compounds are active in vitro against Gram-positive bacteria, yeasts, and fungi. The compounds are particularly active against *Candida albicans* (UC®1392), *Penicillin oxalicum* (UC 1268), and *Saccharomyces cerevisiae* (UC 1342) and have a low toxicity in mammals. (UC is a registered trademark of The Upjohn Company). Specifically this invention concerns both a pure form of a naturally occurring cytosine-containing antibiotic named $10381a_1$ and synthetically derived alkyl esters. In addition, the invention includes a process for culturing and purifying $10381a_1$.

The present invention also provides:

A process for the preparation of Antibiotics 10381b which comprises: fermenting with a strain of *Streptomyces arginensis*, NRRL 15941 and mutants thereof, an aqueous nutrient medium containing an assimilable source of carbon and an assimilable source of nitrogen under aerobic conditions;

A method for promoting growth in meat-producing animals which comprises: administering to the animals an amount of antibiotics 10381b effective to promote growth; and A biologically pure culture of the microorganism *Strepomyces arginensis*, characterized as being essentially the strain identified as NRRL-15941.

The antibiotics of the present invention are produced by a naturally occuring microorganism. As such, these antibiotics may be produced by this organism as it exists in its natural state. The present invention as it is directed to these antibiotics does not encompass any composition thereof as might have or does exist or occur in nature. Rather, the present invention provides for the production and isolation of these antibiotics in a manner rendering them practically useful, e.g., for pharmacological and other anti-microbial purposes.

Accordingly, the antibiotics described herein can be used alone or in combination with other antimicrobial agents to prevent the growth or reduce the numbers of microorganisms in various environments. For example, the compounds could be used to disinfect surfaces or as an additive to paint to prevent excess growth of microorganisms.

DETAILED DESCRIPTION

Antibiotics of formula I where R is hydrogen are obtainable from the cultivation of *S. arginensis*. This antibiotic is designated $10381a_1$. The taxonomy of the organism is given below. The extraction, purification and physicochemical analysis of this antibiotic are also described below.

Compound $10381a_1$ has broad spectrum antibiotic properties having an especially strong growth inhibitory effect upon yeasts and fungi. In addition, $10381a_1$ has less toxicity than blasticidin, a known antibiotic of similar structure.

Antibiotics 10381b of the present invention are also obtainable from the cultivation of *S. arginensis*. The taxonomy of the organism is given below.

Microorganism

The microorganism used for the production of antibiotic $10381a_1$ and antibiotics 10381b is a new species of streptomyces, *Strepomyces arginensis* Dietz sp., NRRL-15941. The organism was isolated from soil screening conducted by The Upjohn Company and was taxonomically characterized by Alma Dietz of The Upjohn Company. A subculture of the organism was deposited under the provisions of the Budapest Treaty on 8 Mar. 1985 in the permanent collection of the Northern Region Research Center, ARS; U.S. Dept. of Agriculture; Peoria, Ill., U.S.A. Its accession number is NRRL-15941.

Color Characteristics

Aerial mycelium is predominantly blue; Melanin-positive. The color pattern on Ektachrome is given in Table 1. Reference color characteristics are given in Table 2. The culture may be placed in the Blue (B) color series of Tresner and Backus. (Appl. Microbiology, 11:335–338, 1963).

Microscopic Characteristics

Spores are in short chains that are slightly curved or that have a simple coil near or at the tip. The spores are adorned with short spines and occasionally with fine hair-like structures. The spores are elliptical and measure 1.2×8 μm.

Growth on Carbon Compounds

The synthetic medium of Shirling and Gottlieb (International al J. Syst. Bacteriol., 16:313–340, 1966), was used for this determination. Growth was good on the positive control (D-glucose), L-arabinose, sucrose, D-xylose, D-mannitol, D-fructose, and rhamnose; and fair on inositol and raffinose. There was no growth on cellulose or on the negative control (synthetic medium ISP-9) without added carbon compound.

Whole Cell Analysis

L-diaminoptmelic acid was detected in the whole cell hydrolysate.

Culture Characteristics

General culture characteristics are given in Table 3.

Temperature

Growth on Bennett's, Czapek's Sucrose, and Maltose-Tryptone Agars was good at 24° C. to 32° C. Optimum growth (good blue aerial growth) was found on Bennett's and Maltose-Tryptone Agars. Growth was fair at 18° C., and moderate at 37° C. There was vegetative growth on Bennett's and Czapek's Sucrose Agars and aerial growth on Maltose-Tryprone Agar at 45° C. There was no growth at 55° C.

*Streptomyces arginensis* was compared to *S. viridochromogenes ss. sulfomycini* ATCC 29776 and *S. viridochromogenes* ATCC 14920. A summary of the taxonomic comparison is presented in Table 4.

Fermentation and Recovery of Antibiotic $10381a_1$ and Antibiotics 10381b

Antibiotic $10381a_1$ (Formula I) and antibiotics 10381b are produced when *S. arginensis* is grown in an aqueous nutrient medium under submerged aerobic conditions. Typically the microorganism is grown in a nutrient medium containing a carbon source and an assimilable nitrogen compound or proteinaceous material. Preferred carbon sources include glucose, brown sugar, sucrose, glycerol, starch, cornstarch, lactose, dextrin, molasses, and the like. Preferred nitrogen sources include corn steep liquor, yeast, autolyzed brewer's yeast with milk solids, soybean meal, cottonseed meal, cornmeal, milk solids, pancreatic digest of casein, distillers' solids, animal peptone liquors, meat and bone scraps, and the like. Combinations of these carbon and nitrogen sources can be used advantageously. Trace metals, for example, zinc, magnesium, manganese, cobalt, iron and the like need not be added to the fermentation medium since tap water and unpurified ingredients are used as medium components.

Production of antibiotic $10381a_1$ and antibiotics 10381b can be induced at any temperature conducive to satisfactory growth of the microorganism preferably between about 20° and 32° C. Ordinarily, optimum production of the antibiotics is obtained in about 2 to 10 days. The medium normally remains weakly basic (pH 7.4–9.0) during the fermentation. The final pH is dependent, in part, on the buffers present, if any, and in part, on the initial pH of the culture medium which is advantageously adjusted to about pH 7.2 prior to sterilization.

When growth is carried out in large vessels and tanks, it is preferable to use the vegetative form, rather than the spore form, of the microorganism for inoculation to avoid a pronounced lag in the production of the antibiotics and the attendant inefficient utilization of the equipment. Accordingly, it is desirable to produce a vegetative inoculum in a nutrient broth culture by inoculating this broth culture with an aliquot from a soil or a slant culture. When a young, active vegetative inoculum has thus been secured, it is transferred aseptically to large vessels or tanks. The medium in which the vegetative inoculum is produced can be the same as, or different from, that utilized for the production of the antibiotics, as long as it is such that adequate growth of the microorganism is obtained.

A variety of procedures can be employed to isolate and purify $10381a_1$ from the fermentation broth, for example, by chromatographic adsorption procedures followed by elution with a suitable solvent, column chromatography, partition chromatography, and crystallization from solvents and combinations thereof.

In the preferred recovery process the clear filtrate is used to extract $10381a_1$. Column chromatography techniques, preferably IRC 50 ($H^+$), and Amberlite XAD-4, (Rohm and Haas; Philadelphia, Pa., U.S.A.) are used to perform the initial purification. Final purification of $10381a_1$ is achieved by counter current distribution.

Bioassays on separate, or combined fractions can be conducted on *Micrococcus luteus* or *Streptococcus pyogenes*. Bioassays are conducted by applying 80 μl of test solution to a ½ inch paper disc and applying the disc to a growing plate of either test organism. A biounit of activity (BU) is defined as the quantity of antibiotic necessary to achieve a 20 mm zone of growth inhibition around the ½ inch paper disc.

Antibiotic $10381a_1$ is an amphoteric compound forming salts with acids, alkaline metals (including ammonia) alkaline earth metals (including magnesium and aluminum, and amtnes). Metal salts can be formed by dissolving $10381a_1$ in water and adding a dilute metal base until the pH is between 7 and 8. Metal salts include sodium, potassium and calcium salts. Amine salts, including those with organic bases such as primary, tertiary, mono-, di-, and polyamines can also be formed using the above-described or other commonly used procedures. Further, ammonium salts can be made by well-known procedures.

Acid salts can be made by neutralizing $10381a_1$ with the appropriate acid to below pH 7.0, and preferably to between pH 2 and 6. Suitable acids for this purpose include hydrochloric, sulfuric, phosphoric, sulfamic, hydrobromic, and the like. Acid and base salts of $10381a_1$ can be used for the same biological purposes as the parent compound.

Antibiotic $10381a_1$ can be esterified under standard esterification conditions. Most preferably compounds of formula I can be treated with alcohol, such as methanol, ethanol, n-propanol, or isopropanol and at reflux temperatures in the presence of hydrogen chloride to yield the $(C_1-C_3)$ alkyl esters of formula I. Both the free base and pharmaceutically acceptable salts as defined above can be used for the same biological purposes as antibiotic $10381a_1$.

It will be apparent to those skilled in the art that compounds of formula I contain several asymmetric carbons. All of the enantiomorphic and stereoisomeric forms of the compounds of formula I are included within the scope of the invention.

Antibiotic $10381a_1$ is active against *Candida albicans* (UC 1392), *Penicillium oxalicum* (UC 1268), *Saccaromyces cerevisiae* (UC 1342), *Strepcococcus pyogenes* (UC 152), and *Strepcococcus faecalis* (UC 694). Therefore, the compounds of formula I are effective for treating bacterial infections in mammals, including humans.

Antibiotics 10381b are isolated from the mycelial cake of the fermentation broth by extraction with methanol. In small scale fermentations (Shake-flask), the methanolic extract is concentrated to dryness and the residue is purified by counter double current distribution (CDCD) alone or followed by silica gel chromatography. The mycelial extract of the cake obtained from large scale fermentation (5000 L fermentor), is concentrated to an aqueous solution which is then extracted with ethyl acetate. The ethyl acetate extracts containing antibiotics 10381b are concentrated to dryness. The oily residue obtained is triturated with ether to yield an amorphous mixture of antibiotics 10381b which are purified further by high performance liquid chromatography (HPLC).

The main components of the 10381 complex have been designated $10381b_2$ and $10381b_3$. Of these two compounds, antibiotic $10381b_2$ was isolated in sufficient quantity and purity to permit biological and chemical characterization.

Antibiotic $10381b_2$ is active against Gram-positive organisms and anaerobes (*Clostridium perfrigens, Bacteroides fragilis*). It is also active against *Staphylococcus aureus* resistant to other antibiotics (*Staphylococcus aureus* UC 3665, *Staphylococcus aureus* UC 6685). (UC is a registered trademark of The Upjohn Company). Therefore, antibiotics 10381b are effective for treating bacterial infections in mammals, including humans.

Various compositions of the antibiotics of the present invention are presented for administration to humans and animals in unit dosage forms, such as tablets, capsules, pills, powders, granules, sterile parenteral solutions or suspensions, eye drops, oral solutions or suspensions, and water-in-oil emulsions containing suitable quantities of the antibiotics.

For oral administration, either solid or fluid unit dosage forms can be prepared. For preparing solid compositions such as tablets, the desired antibiotic is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the antibiotic with an inert pharmaceutical diluent and filling the mixture into a hard gelatin capsule of appropriate size. Soft gelatin capsules are prepared by machine encapsulation of a slurry of the antibiotic with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the antibiotic and a sterile vehicle, water being preferred. The antibiotic, depending on the vehicle and concentration used, can be either suspended or dissolved in the vehicle. In preparing solutions, the antibiotic can be dissolved in water for injection and filtered sterilized before filling into a suitable vial or ampoule and sealing. Advantageously, adJuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the antibiotic is suspended in the vehicle instead of being dissolved and sterilization cannot be accomplished by filtration. The antibiotic can be sterilized by exposure to ethylene oxide before suspending in the sterile vehicle. Advantageously, a surfactant or wetting agent is included in the composition to facilitate uniform distribution of the antibiotic.

Additionally, a rectal suppository can be employed to deliver the antibiotic. This dosage form is of particular interest where the mammal cannot be treated conveniently be means of other dosage forms, such as orally or by insufflation, as in the case of young children or debilitated persons. The antibiotic can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 gm.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of antibiotic is employed in treatment. The dosage of the antibiotic for treatment depends on many factors that are well known to those skilled in the art. They include for example, the route of administration and the potency of the particular antibiotic. A dosage schedule for humans of from about 1 to 2 grams of the antibiotic in a single dose, administered parenterally or in the compositions of this invention, are effective for treating bacterial infections. More specifically, the single dose is about 2 grams of the antibiotic. The oral and rectal dose is from about 1 to 2 grams in a single dose. More specifically, the single dose is about 2 grams of the antibiotic.

The antibiotics of the present invention may also be used to promote growth in meat-producing animals such as broiler chicks, swine and cattle. For example, the antibiotics 10381b were mixed with the feed of broiler chicks (NRC approved diet) to a dosage level of about eleven parts per million (or eleven mg/kg). Over a two-week period, each chick (one-day old) ate ad libitum about 20 g of feed per day. Therefore, it was calculated that each chick ingested about 220 mcg of the antibiotics 10381b per day and that the mean growth index of the antibiotics was greater than three and significantly greater than zero. (The mean growth index measures the improvement in growth over controls (chicks given feed without addition of drug).) An example of the use of the antibiotics of the present invention to promote growth in swine is given below.

Variations in the above amounts and procedures for the use of the antibiotics of the present invention to promote growth in meat-producing animals would be known to one of ordinary skill in the art. For broiler chicks, the preferred concentrations of antibiotics 10381b is from about 0.5 to about 11 mg/kg of feed. For swine, the preferred concentration of antibiotics 10381b is from about 10 to about 55 mg/kg of feed.

DESCRIPTION OF THE PREFERRED EMBODIMENTS

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

In examples 2, 3 and 4, antibiotic production and purification are measured by a microbiological disc plate assay procedure with *Micrococcus luteus* and *Streptococcus pyogenes* as the assay organisms. Thin-layer chromatography is performed on cellulose (Brinkman Cell 300); pH 7.0, 0.1M phosphate buffer or silica gel (Brinkman's Polygram SIL-N-HR) plates using chloroform-methanol (95:5 or 100:10 v/v) as the mobile phase. Bioautography is performed on *M. luteus* or *S. pyogenes*.

EXAMPLE 1

A. Fermentation

A soil stock of *Streptomyces arginensis*, NRRL-15941 is cultured on Hickney-Tresner Agar and stored at 4° C. Samples are homogenized in water and replated on Hickney-Tresner Agar. After 7 days of incubation at 28° C., the growth is sufficient for a seed culture inoculum.

Seed cultures are grown in seed medium (SSM.1) containing per liter of tap water: blackstrap molasses 5.8 g, Difco peptone 10 g, Difco yeast extract 4 g, dextrin 4 g, L-asparagine 0.2 g, $CoCl_2.6H_2O$ 1 mg; the medium is adjusted to pH 7.2 with KOH before sterilization. The SSM.1 is dispensed into plain 500 ml wide-mouth Erlenmeyer flasks (capped with 2 milk filters) at 100 ml/flask and autoclaved for 30 minutes at 121° C., 15 psi. Flasks are inoculated with homogenized ized agar plugs at a rate of 0.5–1 plug/flask and shaken (250 rpm, 2.5" stroke) for 3 days at 28° C. The harvest pH is 8.3.

The seed cultures are fermented in media containing in amounts per liter of tap water: soybean meal 20 g, brewer's yeast 2 g, Cerelose 20 g (added as 50% solution after autoclavtng); the medium is adjusted to pH 7.2 before sterilization . The medium is dispensed, sterilized and shaken as described above. The inoculation rate is 5 ml/100 ml of seed culture. Fermentation conditions are for 3 days at 28° C.

B. Purification for a 10 liter fermentation beer.

The beer is filtered using a filter aid as required and the solid cake is washed in water in an amount one-tenth the volume of the filtrate filtered and added to the beer-filtrate which is saved.

A one liter column of IRC-50 ($H^+$) is prepared and the filtrate mixture is adjusted to pH 8.5 using ammonium hydroxide. The filtrate is passed through the column at a rate of 50–60 ml/minute and collected as a single fraction.

The antibiotic fraction is eluted off the IRC-50 column using 2N aqueous ammonium chloride collecting 2 liter-fractions and combining active fractions.

An 800 ml column of Amberlite XAD-4 is prepared. The preceding ammonium chloride eluate is adjusted to a pH of 8.0 using ammonium hydroxide and passed over the column at a rate of 50–60 ml/minute. The column is washed with 3 liters of water. The active fraction is eluted off by 5 elutions with methanol-water 70:30 w/v. The 5 elutions of methanol-water are concentrated to an aqueous solution, freeze-dried and tested for activity.

The various filtrate or eluant solutions are bioassayed as previously described. A typical assay is presented in Table 5. The fractions from the IRC-50 column are being tested against *M. luteus*.

Final purification of $10381a_1$ is achieved by countercurrent distribution (CCD). Active fractions from an Amberlite XAD-4 column are dissolved in both phases of the solvent system consisting of 1-butanol/pH 7.0 phosphate buffer and distributed in an all-glass countercurrent distribution apparatus. After approximately 500 transfers, the bioactivity of the CCD-fractions is determined and the active fractions concentrated to an aqueous solution which is freeze-dried. The residue is dissolved in water and pH adjusted to 8.

The aqueous solution is passed through a one liter column of Amberlite XAD-4, and washed three times with three one-liter portions of water (wash 1, 2 and 3). The column is then eluted with methanol-water (70:30 v/v). The aqueous-methanoltc fractions are assayed for antimicrobial activity (Table 6). Biologically-active fractions are combined, concentrated to an aqueous solution and freeze-dried to yield pure antibiotic $10381a_1$. The physicochemical properties of $10381a_1$ are presented in Table 7. The spectrum of $10381a_1$'s antimicrobial activity is presented in Table 8.

C. Isolation of Antibiotics 10381b from Shake-Flask or 10 L-Tank Fermentations.

The fermentation beer is filtered using a filter aid as required and the solid cake is washed with one-tenth beer volume of water.

The clear filtrate and wash are combined.

The cake is triturated four times with 1.5 l portions of methanol. The methanolic extracts are assayed (Table 9).

The active fractions are combined and concentrated to dryness to give Preparation A which is used as the starting material for the isolation and purification of antibiotics 10381b.

EXAMPLE 2

Isolation of antibiotics 10381b from Preparation A by Counter Double Current Distribution and Silica Gel Chromatography.

A. Counter Double Current Distribution:

Two lots of Preparation A, prepared as described in Example 1 (Part C), are combined (26.7 g and 18.6 g) and dissolved in both phases (125 ml of each phase) of the solvent system cyclohexane-ethyl acetate-95% ethanol-water (1:1:1:1 v/v). The solution is added in tubes 20–25 of the upper side of the counter double current apparatus (the side where the lower phase enters the machine). The following transfers are run:

1) 25 transfers (fractions are not collected);

2) 45 transfers (upper phase is collected); and 3) 100 transfers (both phases are collected).

Fractions are analyzed by bioactivity determination and by bioautography of developed tlc plates on an antibiotic-sensitive microorganism (bio-tlc). The following pools are made. The solution in each pool is concentrated to an aqueous and freeze-dried to yield the following preparations:

Pool I: (fractions: lower collector 5-24) prep. 84.1 (28.48 g);

Pool II: (fractions: lower collector 25-79) prep. 84.2 (1.85 g); and

Pool III: (fractions: lower collector 80-100; lower machine 50-0; upper machine 1-20) prep. 84.3 (0.25 g).

Thin layer chromatographic analysis (Brinkman's silica gel; chloroform-methanol 95:5 (v/v); bioautography on $M.$ $luteus$ sens) gives the following $R_f$ values: 0.8 ($10381b_5$); 0.6 ($10381b_4$); 0.5 ($10381b_3$); 0.2 ($10381b_2$); and 0 ($10381b_1$).

The potency values (Bu/mg) of the preparations versus $M.$ $luteus$ sens are as follows: 2 (Prep. 84.1); 64 (Prep. 84.2); and 256 (Prep. 84.3).

B. Silica Gel Chromatography

The column is prepared from 600 g of silica gel in chloroform-methanol (97:3 v/v). Preparations 84.2 and 84.3, obtained as described above, are combined and triturated with 31 ml of absolute methanol. Insoluble, bioinactive material is separated by filtration (600 mg). The filtrate is mixed with 60 g of filter aid and 970 ml of chloroform. The mixture is concentrated to a dry powder. This residue is added in the top of the column which is eluted as follows. Fractions of 20 ml are collected:

1) Chloroform-methanol (97:3 v/v): Fractions 1–837;

2) Chloroform-methanol (94:6 v/v): Fractions 838–1285; and

3) Chloroform-methanol (90:10 v/v): Fractions 1286–1600.

Fractions are analyzed by bioactivity and by bto-tlc. The following pools are made. Each pool is concentrated to dryness to give the following preparations:

Pool I: (fractions 230–299) prep. 106.1 (30 mg);

Pool II: (fractions 300–500) prep. 106.2 (40 mg);

Pool III: (fractions 855–930) prep. 106.3 (40 mg); and

Pool IV: (fractions 931–1000) prep. 106.4 (40 mg).

Thin layer chromatographic analysis (Silica gel; chloroformmethanol (95:5); bioautography on $M.luteus$) gives the following $R_f$ values: 0.5 ($10381b_3$); and 0.2 ($10381b_2$).

The potency values (Bu/mg) of the preparations versus $S.$ $pyogenes$ are as follows: 128 (Prep. 106.1); 100 (Prep. 106.2); >1024 (Prep. 106.3); and 380 (Prep. 106.4). The potency values (Bu/mg) of the preparations versus $M.$ $luteus$ sens are as follows: 96 (Prep. 106.1); 64 (Prep. 106.2); 384 (Prep. 106.3); and 96 (Prep. 106.4).

EXAMPLE 3

Isolation of antibiotics 10381b from Preparation A by Counter Double Current Distribution. (Solvent: Cyclohexane-ethyl acetate-acetone-water (1:2:2:1 v/v).

Three lots of Preparation A, prepared as described in Example 1 (Part C), are combined (20.5 g, 21.1 g and 20.8 g) and dissolved in both phases of the above system (155 ml of each phase). The solution is added in tubes 18–25 of the upper side of the counter current distribution apparatus (the side where the lower phase enters the machine). The following transfers are run:

1) 68 transfers (the upper phase is collected); and 2) 100 transfers (both phases are collected).

The distribution is analyzed by bioactivity determination and bio-tlc. The following pools are made. Each pool is concentrated to an aqueous and freeze-dried to give the following preparations:

Pool I: (fractions: lower collector 1-30) prep. 91.1 (34.8 g);

Pool II: (fractions: lower machine 30-0; upper machine 1-30) prep. 91.2 (240 mg);

Pool III: (fractions: upper machine 35-50; upper collector 170 -80) prep. 91.3 (300 mg); and Pool IV: (fractions: upper collector 79-27) prep. 91.4.

Thin layer chromatographic analysis, (silica gel; chloroformmethanol 95:5; bioautography on $M.$ $luteus$) gives the following $R_f$ values: 0.2 ($10381b_2$). The above tlc shows that prep. 91.3 contains mainly $10381b_2$ and traces of $10381b_1$, and has a potency of ca. 3000 Bu/mg vs. $S.$ $pyogenes$.

EXAMPLE 4

Isolation of Antibiotics 10381b from a 5000 L Fermentation.

A. The whole beer (harvest pH 6.9) is filtered using CELATOM FW 40 as a filter aid. The cake is washed with 5000 L of water and then triturated four times with 600 L of methanol each time. The four methanolic extracts are pooled and concentrated to a volume of 90 L. The aqueous concentrate (pH 7.0) is then extracted three times with equal volumes of ethyl acetate. The three ethyl acetate extracts are combined and concentrated to a volume of 15.5 L (assay: ca. 1000 Bu/ml, $S.$ $pyogenes$) to give Preparation B.

Preparation B is mixed with 60 L of Skellysolve B. The mixture is allowed to stand at room temperature for 20 hours. Insoluble material (antibiotics 10381b) is isolated by filtration over a filter containing filter aid. The filtrate is discarded. The cake, containing antibiotics 10381b, is washed with Skellysolve B and then slurried four times with 4 L portions of methanol. The four methanolic extracts are combined and the solution is concentrated to dryness to give Preparation C.

Preparation C is triturated with ether (ca. 2 L). Insoluble material is isolated by filtration and dried (47.3 g) and assayed ca. 2000 Bu/mg.

B. Purification of Preparation C by High Performance Liquid Chromatography (HPLC). (Instrument: Waters Prep 500A; Support: Waters C-18 Reverse Phase Silica-Packed Columns; Mobile Phase: Acetonitrile-Water (40:60 v/v); and Flow Rate: 150 ml/min).

Preparation C (1.0 g), obtained as described above, is stirred with 100 ml of acetonitrile and 150 ml of water for 2 hours. Insoluble material is separated by filtration (258 mg). The filtrate is injected into the column. The chromatography is followed by a UV detector. In addition selected fractions (150 ml each) are tested for bioactivity and analyzed by tlc (silica gel; chloroform-methanol 10 v/v; bioautography on *Micrococcus luteus*). Fractions 63–96, containing 10381b$_2$ only, are combined and concentrated to an aqueous solution (1600 ml). This solution is then extracted three times with ml portions of ethyl acetate each time, The ethyl acetate extracts are combined, dried over sodium sulfate and concentrated to dryness to give 129 mg of product. The product is dissolved in 2.5 ml of dimethylsulfoxide and 2.5 ml of methanol. This solution then mixed with 200 ml of ether. The precipitated material (61 mg) is characterized. Results are reported below.

C. Physical characteristics: The physical characteristics of 10381b$_2$ are presented in Table 10. The spectrum of 10381b$_2$'s antimicrobial activity is presented in Table 11.

EXAMPLE 5

Antibiotic 10381a$_1$ Hydrochloride

Antibiotic 10381a$_1$, 300 mg is dissolved in 10 ml of 1N methanolic hydrogen chloride. The solution is clarified by filtration over a sintered glass filter and mixed with 100 ml of acetone and 50 ml of ether. The precipitated colorless material is isolated by filtration and dried. Physicochemical data for 10381a$_1$ hydrochloride are presented in Table 12.

EXAMPLE 6

Antibiotic 10381a$_1$ Methyl Ester Hydrochloride

Antibiotic 10381a$_1$, 500 mg is dissolved in 20 ml of 0.8N methanolic hydrogen chloride. The solution is kept at reflux for 3 hours and then cooled and clarified by filtration over a sintered glass filter. The clear solution is mixed with 200 ml of acetone and 50 ml of ether. The precipitated colorless material is isolated by filtration and dried. Physicochemical data for 10381a$_1$ methyl ester hydrochloride is presented in Table 13.

Utilizing a procedure similar to that described in Example 3 but substituting ethanolic or propanolic hydrogen chloride, there is obtained the corresponding ethyl or propyl ester.

EXAMPLE 7

Use of Antibiotics 10381b to Promote Growth in Swine

Facilities: Each trial was conducted in a facility where heating and ventilation equipment were adequate to maintain a desirable nursery environment. Each pen is equipped with a self-feeder and a nipple type drinker. The floor of each pen is solid concrete except for 0.74 m$^2$ of expanded metal slats over a flush gutter at one end of the pens for manure removal.

Animals: Equal numbers of healthy female and castrate male Hampshire X Yorkshire crossbred, weaned pigs five to six weeks of age were used for each trial. The experimental unit consisted of a pen of four pigs, two females and two males. Within each trial, pigs were assigned to blocks of pens by weight group and randomly allotted to individual pens within the blocks (same procedure followed for both sexes). Blocks of pens were randomly assigned to positions within the nursery and treatments were randomly assigned to pens of pigs within the block.

Diets and Treatments: A corn soybean meal based diet with approximately 18% crude protein, was the basal diet to which the drug was added to provide the treatments.

Appropriate quantities of 10,381b were premixed into soybean mill feed to a concentration of 44 grams per kilogram of premix. The premix was then mixed with the diet to attain a finished feed level of 55 mg of drug activity per kilogram of diet.

Analysis of Data: Variables of interest are gain, expressed as average daily gain (ADG), feed efficiency, expressed as feed consumed divided by gain (F/G), and growth index (GI) which is calculated by summing the within block improvements in ADG and F/G with each weighted equally.

The responses from the drug for each variable was calculated within each weight block relative to controls, e.g.:

Improvements in ADG-100 (ADG of treated—ADG of Control) ADG of Control

A t-test was used to evaluate the probability of chance differences. Estimates of variance were obtained from analysis of variance using a model with trials and blocks within trials.

Following the swine performance screen procedures, 256 Yorkshire X Hampshire crossbred pigs were fed diets which contained either no drug of 10,381b at 55 mg/kg for 21 days. Drug treatment was represented in eight blocks (four pigs per pen) per trial in four trials conducted over 8 months. A growth index (GI) was calculated from the within block comparisons to measure improvements in gain and feed efficiency for the compound. To pass this screen a compound must have a GI of at least 7.5 and be significantly different from zero at P<0.10.

10,381b was acceptable with a GI equal to 29.52 with P=0.004.

From Table 14, it can be seen that the growth index for 10,381b is positive and exceeds the minimum criteria of 7.5. From Table 15, it can be seen that the probability that this response is due to chance is less than p<0.10.

TABLE 1

Color characteristics[1] on Ektachrome[2] of *Streptomyces arginensis* NRRL-15941.

| Agar Medium | | Chip | Color |
| --- | --- | --- | --- |
| Bennett's | S | 190 | light blue gray |
| | R | 77 | moderate yellow brown |
| Czapek's sucrose | S | 263 | white |
| | R | 70 | light olive |
| Maltose-tryptone | S | 190 | light blue gray |
| | R | 81 | dark grayish yellowish brown |
| Peptone-iron | S | 81 | dark grayish yellowish brown |
| | R | 81 | dark grayish yellowish brown |
| 0.1% Tyrosine | S | 191 | bluish gray |
| | R | 76 | light yellowish brown |
| Casein starch | S | 191 | bluish gray |
| | R | 77 | moderate yellowish brown |

S = surface, R = reverse.
[1]Growth on media in tubes was photographed after seven days incubation at 28° C. Color was determined by comparison with NBS color chips. (Kelly, K. L., and D. B. Judd. 1976. Color. Universal Language and Dictionary of Names. NBS Spec. Publ. 440. Superintendent of Documents, U.S. Government Printing Office, Washington, D.C. 20942; and SRM 2106. 1958. ISCC-NBS Centroid Color Charts. Office of Standard Reference Material, Room B311, Chem. Building, National Bureau of Standards, Washington, D.C. 20234.)
[2]Dietz, A. and Thayer, D. W. (ed.) 1980. SIM Special Publ. No. 6. Soc. for Ind. Microbiol., Arlington, VA.

TABLE 2

Reference color characteristics[1] *Streptomyces arginensis* NRRL-15941.

| Agar Medium | | Chip | Color |
|---|---|---|---|
| Bennett's | S | 184 | very pale blue |
| | R | 87 | moderate yellow |
| | P | — | |
| Czapek's sucrose | S | 7 | pale pink |
| | | 9 | pink white |
| | R | 33 | brownish pink |
| | P | — | |
| Maltose-tryptone | S | 10 | pinkish gray (edge) |
| | | 60 | light grayish brown (center) |
| | R | 77 | moderate yellowish brown |
| | P | 90 | grayish yellow |
| Yeast extract- malt extract (ISP-2) | S | 190 | light bluish gray |
| | R | 88 | dark yellow |
| | P | 90 | grayish yellow |
| Oatmeal (ISP-3) | S | 189 | bluish white |
| | R | 105 | grayish greenish yellow |
| | P | 93 | yellowish gray |
| Inorganic salts starch (ISP-4) | S | 184 | very pale blue |
| | R | 105 | grayish greenish yellow |
| | P | — | |
| Glycerol- asparagine (ISP-5) | S | 190 | light bluish gray |
| | R | 105 | grayish greenish yellow |

S = surface, R = reverse, P = pigment.
[1]Color determination was made on growth on plates incubated 14 days at 28° C. Color was determined by comparison with NBS color chips. (Kelly, K. L., and D. B. Judd. 1976. Color. Universal Language and Dictionary of Names. NBS Spec. Publ. 440. Superintendent of Documents, U.S. Government Printing Office, Washington, D.C. 20942; and SRM 2106. 1958. ISCC-NBS Centroid Color Charts. Office of Standard Reference Material, Room B311, Chem. Building, National Bureau of Standards, Washington, D.C. 20234.)

TABLE 3

Culture characteristics[1] - general *Streptomyces arginensis* NRRL-15941.

| Medium[2] | | Culture Characteristics |
|---|---|---|
| *Agar* | | |
| Peptone-iron | S | brown vegetative growth |
| | R | brown |
| | P | brown |
| | O | melanin-positive |
| Calcium malate | S | pale gray |
| | R | pale gray |
| | P | — |
| | O | malate solubilized |
| Glucose asparagine | S | pale gray |
| | R | pale cream |
| | P | — |
| Skim milk | S | pale tan vegetative |
| | R | orange-tan |
| | P | orange-tan |
| | O | casein not solubilized |
| Tyrosine | S | trace gray |
| | R | brown |
| | P | pink-brown |
| | O | tyrosine not solubilized |
| Xanthine | S | very slight trace gray |
| | R | pale yellow-tan |
| | O | xanthine solubilized |
| Nutrient starch | S | very slight trace grey |
| | R | pale yellow |
| | P | pale yellow |
| | O | starch solubilized |
| Yeast extract malt extract | S | pale blue-white |
| | R | yellow tan |
| | P | yellow tan |
| Peptone- yeast extract- | S | tan vegetative |
| | R | tan brown |
| iron (ISP-6) | P | tan |
| | O | melanin-doubtful |
| Tyrosine (ISP-7) | S | pale blue |
| | R | gray brown |
| | P | trace tan |
| | O | melanin-negative |
| *Gelatin* | | |
| Plain | S | tan surface ring |
| | P | tan |
| | O | trace liquefaction |
| Nutrient | S | tan surface ring |
| | P | tan |
| | O | no liquefaction |
| *Broth* | | |
| Synthetic nitrate | S | wide surface ring with trace pink aerial growth |
| | P | pale yellow |
| | O | flocculent throughout and at base no reduction |
| Nutrient nitrate | S | no growth |
| | P | brown (1 tube), tan (2 tubes) |
| | O | flocculent at base no reduction |
| Litmus milk | S | brown ring |
| | P | — |
| | O | no change in litmus pH 6.3 (control, 6.5) |

S = surface, R = reverse, P = pigment, O = other characteristics
[1]DIetz, A. and Thayer, D. W. (ed.) 1980. SIM Special Publ. No. 6. Soc. for Ind. Microbiol., Arlington, VA.
[2]Growth on media in tubes was photographed after seven days incubation at 28° C. Color was determined by comparison with NBS color chips. (Kelly, K. L., and D. B. Judd. 1976. Color. Universal Language and Dictionary of Names. NBS Spec. Publ. 440. Superintendent of Documents. U.S. Government Printing Office, Washington, D.C. 20942; and SRM 2106. 1958. ISCC-NBS Centroid Color Charts. Office of Standard Reference Material, Room B311, Chem. Building, National Bureau of Standards, Washington, D.C. 20234.)

TABLE 4

Comparison of *S. arginensis* NRRL-15941 with *S. viridochromogenes* ss. *sulfomycini* ATCC 29776 and *S. viridochromogenes* ATCC 14920[1].

| Characteristic | NRRL-15941 | ATCC 29776 | ATCC 14920 |
|---|---|---|---|
| Aerial mass color | + | + | +, − |
| blue | | | |
| Colony reverse color Peptone-iron agar | brown | brown | ? |
| *Melanoid pigments* | | | |
| Peptone-yeast- iron agar | − | − | − |
| Tyrosine agar | − | +, − | +, − |
| Utilization of sucrose | ++ | ++ | doubtful |
| *Spore chain* | | | |
| morphology | short loose coil | moderate compact spiral | long open spiral |
| (spores/chain) | 10–15 | <50 | >50 |
| Spore surface | spiny | spiny | spiny |
| Production of 10381a | + | − | not tested |

[1]Dietz, A. and Thayer, D. W. (ed.) 1980. SIM Special Publ. No. 6. Soc. for Ind. Microbiol., Arlington, VA.

TABLE 5

Bioassay

| | ZONES (mm) Dilution | | | | |
|---|---|---|---|---|---|
| | FS | ½ | ¼ | ⅛ | ¹⁄₁₆ |
| Filtrate | 26 | 23 | 21 | 18 | Trace |
| Spent | 0 | 0 | 0 | 0 | 0 |
| Wash | 0 | 0 | 0 | 0 | 0 |
| $NH_4Cl$ (9L) | 25 | 22 | 19 | 15 | Trace |

TABLE 6

Bioassay

| | Amount | Full Strength | 1/10 (zone of inhibition vs. *M. luteus*) | 1/100 |
|---|---|---|---|---|
| SPENT | | 0 | 0 | 0 |
| WASH-1 | | 0 | 0 | 0 |
| WASH-2 | | 16(1) | 0 | 0 |
| WASH-3 | | 0 | 0 | 0 |
| Methanol-1 | 500 ml | 19 | 0 | 0 |
| Methanol-2 | 500 ml | 44 | 35 | 25 |
| Methanol-3 | 500 ml | 35 | 25 | 0 |
| Methanol-4 | 500 ml | 27 | traces | 0 |
| Methanol-5 | 1,000 ml | 23 | — | — |

TABLE 7

CHARACTERIZATION OF ANTIBIOTIC 1038a₁

1. Appearance: Colorless amorphous material.
2. Solubility: Soluble in water and lower alcohols. Insoluble in acetone, ethyl acetate, ether and chlorinated or saturated hydrocarbon solvents.
3. Molecular Composition: $C_{18}H_{28}N_8O_5$ Calcd molecular weight: 436.2183
Found (HR-FAB/MS): 436.21776.
4. $[\alpha]^{25}D$: +44° (C., 0.55, water).
5. Melting Point: Decomposition at ca. 218° C.

6. UV Spectrum:

| λmax (nm) | α | ε | Solvent |
|---|---|---|---|
| 268 | 14.02 | 6100 | water |
| 268 | 14.25 | 6200 | 0.1N NaOH |
| 276 | 19.55 | 8500 | 0.1N HCl |

7. The $R_f$ values of Antibiotic 10381a₁ using paper chromatography and various solvent systems are listed below:

PAPER CHROMATOGRAPHIC MOBILITIES OF ANTIBIOTIC 10381A₁

| No. (#) | Solvent Sytem[1] | $R_f$ |
|---|---|---|
| 1 | 1-Butanol:water, 21:4 | 0 |
| 2 | #1 with 0.25% p-toluene sulfonic acid | 0.2 |
| 3 | 1-Butanol:acetic acid:water, 2:1:1 | 0.2 |
| 4 | #1 with 2% piperidine | NZ |
| 5 | 1-Butanol:water, 1:24 | 0.7 |
| 6 | #5 with 0.25% p-toluene sulfonic acid | 0.8 |
| 7 | 0.1 M potassium phosphate, pH 7.0 | 0.9 |
| 8 | 0.075 N ammonium hydroxide saturated with methyl isobutyl ketone | 0.9 |
| 9 | Benzene:methanol:water, 1:1:2 (upper phase) | 0 |
| 10 | #1 with 2% p-toluene sulfonic acid | 0.2 |
| 11 | Methanol:15% NaCl, 4:1 | 0.5 |

[1]Liquid = Liquid ratios are v/v; solid percentages are w/v.
NZ = No zone.

9. IR Band Tabulation:

IR BAND TABULATION OF ANTIBIOTIC 10381A₁, METHYL ESTER

| Band Frequency | Intensity | Type | Band Frequency | Intensity | Type |
|---|---|---|---|---|---|
| 3197.0 | 13 | BRD | 1605.7 | 6 | BRD |
| 2953.9 | 0 | BRD M | 1522.7 | 17 | AVG |
| 2916.3 | 0 | BRD M | 1490.9 | 14 | AVG |
| 2868.1 | 3 | SH M | 1464.9 | 9 | AVG M |
| 2854.6 | 2 | AVG M | 1411.8 | 32 | SH |
| 2735.0 | 59 | SH M | 1391.6 | 23 | SH |
| 2681.0 | 64 | SH M | 1378.1 | 13 | AVG M |
| 1649.1 | 4 | BRD | 1354.9 | 37 | SH |
| 1296.1 | 39 | SH | 944.1 | 62 | AVG |
| 1280.7 | 36 | AVG | 896.8 | 65 | SH |
| 1229.6 | 38 | AVG | 868.9 | 57 | AVG |
| 1203.5 | 45 | AVG | 826.4 | 47 | AVG |
| 1184.2 | 53 | SH | 788.8 | 37 | AVG |
| 1117.7 | 44 | AVG | 778.2 | 41 | SH |
| 1070.4 | 33 | AVG | 721.3 | 33 | AVG M |
| 983.6 | 59 | AVG | | | |

Band Frequency: Band frequencies in wavenumbers ($CM^{-1}$)
Intensity: Intensity in percent transmittance (% T)
Data Type in Local Peak Region: BRD = Broad; AVG = Average; SHP = Sharp; SH = Shoulder.
M: Possible interference from mineral oil.

TABLE 8

ANTIBACTERIAL SPECTRUM OF ANTIBIOTIC 10381A₁[1]

| Organism | Culture # | Zone of Inhibition (mm) |
|---|---|---|
| *Bacillus subtilis* | UC 564 | 0 |
| *Staphylococcus aureus* | UC 80 | 16h |
| *Staphylococcus aureus* | UC 3665 | 0 |
| *Micrococcus luteus* | UC 130 | 32 |
| *Micrococcus luteus* | UC 3383 | 32 |
| *Klebsiella pneumoniae* | UC 57 | 0 |
| *Escherichia coli* | UC 51 | 0 |
| *Salmonella schottmuelleri* | UC 126 | 0 |
| *Proteus vulgaris* | UC 93 | 0 |
| *Mycobacterium avium* | UC 159 | 17 |
| *Penicillium oxalicum* | UC 1268 | 36 |
| *Pseudomonas aeruginosa* | UC 95 | 0 |
| *Rhodopseudomonas sphaeroides* | UC 3238 | 33 |
| *Streptococcus pyogenes* | UC 152 | 25 |
| *Clostridium perfrigens* | UC 6509 | 18 |
| *Bacteroides fragilis* | UC 6513 | 21 |
| \*Staphylococcus aureus | UC 6685 | 0 |
| \*Staphylococcus epidermidis | UC 719 | tr |
| \*Streptococcus faecalis | UC 221 | 10 vl |
| \*Streptococcus pneumoniae | UC 9207 | tr |
| \*Hemophilus influenzae | UC 6483 | 10 |
| \*Serratia marcescens | UC 6888 | 0 |
| \*Neisseria gonorrhoeae | UC 3065 | tr |
| \*Candida albicans | UC 1392 | 12 |
| *Saccharomyces cerevisiae* | UC 1342 | 31 |
| *Bordetella bronchiseptica* | UC 6481 | 0 |
| *Pasteurella hemolytica* | UC 6531 | 0 |

[1]Assays marked * used ¼ inch (6.35 mm) discs and 20 µl samples.
All other assays used ½ inch (12.7 mm) discs and 80 µl samples.
h = hazy; vl = very light; tr = trace. Assay procedures are described in Hanka, L. J., M. R. Burch and W. T. Sokolski. Psicofuranine. IV. Microbiological assay. Antibiot. and Chemoth. 9:432–435 (1959).

TABLE 9

Bioassay: Filtration, Extraction Cake

1. *S. lutea*-sensitive

| | ZONES (mm) | | | | |
|---|---|---|---|---|---|
| | FS | ½ | ¼ | ⅛ | 1/16 |
| Clear beer | 26 | 23 | 21 | 18 | Trace |
| Methanol-1 | 29 | 27 | 24 | 21 | 17 |
| Methanol-2 | 27 | 25 | 23 | 20 | 17 |
| Methanol-3 | 24 | 21 | 19 | 17 | — |
| Methanol-4 | 20 | 15 | 0 | 0 | 0 |

2. *S. pyogenes*

| | ZONES (mm) | | | | |
|---|---|---|---|---|---|
| | FS | ½ | ¼ | ⅛ | 1/16 |
| Clear beer | 25 | 23 | 21 | 18.5 | 17.5 |
| Methanol-1 | 30.5 | 30 | 28 | 25.5 | 23 |
| Methanol-2 | 29.5 | 28.5 | 26 | 24 | 22 |
| Methanol-3 | 27 | 25 | 24 | 22 | — |
| Methanol-4 | 25 | 22.5 | 21 | 19 | — |

TABLE 10

CHARACTERIZATION OF ANTIBIOTIC 10381b$_2$

| | |
|---|---|
| Appearance: | Amorphous colored solid. |
| Solubility: | Soluble in dimethylformamide, dimethylsulfoxide and lower alcohols. Less soluble in ethyl acetate, acetone and acetonitrile. Insoluble in ether and saturated hydrocarbon solvents. |
| Analytical Data: | C, 48.33; H, 4.58; N, 15.14; S, 5.16; O (by difference, 26.79). |
| Empirical formula: | From the analytical values, the formula of $C_{25.5}H_{28.5-29}N_{6.5}O_{10.5}S$ is derived. Assuming that the molecule contains two sulfur atoms, the molecular formula for 10381b$_2$ becomes $C_{51}H_{57}N_{13}O_{21}S_2$ (molecular weight 1225). |
| Melting point: | At approximately 195° C., the material begins to decompose with evolution of gas. |
| Ultraviolet Spectrum: | ($\lambda_{max}$, methanol): 243, 316. |
| Infrared Spectrum: | (cm$^{-1}$, mineral oil mull): 2965.5, 2851.6, 1465.7, 1495.6, 1377.0, 1663.5, 1526.5, 1633.6, 3337.7, 1368.3, 1341.3, 721.2, 1197.6, 1082.0, 1307.6, 1021.2, 1039.5, 749.2, 1291.2, 1249.7, 1122.5, 1102.2, 889.0, 1147.5, 997.0. |
| Antibacterial Spectrum: | Antibiotic 10381b$_2$ is active mainly vs. G+ organisms and anaerobes (*Clostridium perfrigens*; *Bacteroides fragilis*). It is also active vs. *Staphylococcus aureus* resistant to other antibiotics (*Staphylococcus aureus* UC 3665; *Staphylococcus aureus* UC 6685). |
| Antibacterial in vitro testing: | In vitro testing results of antibiotic 10381b$_2$ vs. G+ and G− organisms are in Table 7. |
| Paper Chromatography: | R$_f$ (solvent system): 0.5–0.9 (streaking) (1-butanol/water 84/16); 0.5–0.9 (streaking) (1-butanol/water 84/16 + 0.25% p-toluene-sulfonic acid); 0.9 (1-butanol/acetic acid/water 2/1/1); 0.9 (1-butanol/water 84/16 + 2% piperidine); 0.1–0.5 (streaking) (1-butanol/water 4/96); 0.1–0.5 (streaking) (1-butanol/water 4/96 + 0.25% p-toluene-sulfonic acid); 0.1–0.5 M potassium phosphate pH 7.0); 0.1–0.3 (water/methyl isobutyl ketone/ammonia 200/20/−1); 0.9 (toluene/methanol/water 1/1/2); 0.9 (1-butanol/water 84/16 + 2.0% p-toluene-sulfonic acid); 0.9 (methanol/15% NaCl (H$_2$O) 4/1). |
| In vivo testing of antibiotic 10381b$_2$: | Antibiotic 10381b$_2$ was tested in vivo vs. *Streptococcus pyogenes* and *Staphylococcus aureus*-induced mouse mastitis. The antibiotic protected *S. pyogenes*-infected mice when administered subcutaneously with a CD$_{50}$ of 1.25 mg/Kg. It was active in the *S. aureus*-induced mouse mastitis test with PD$_{50}$ of 1.8 (vs. mastitis) and 6.2 (vs. *S. aureus*) mg/kg. |
| Testing of antibiotic 10381b$_2$ complex for growth promotion: | Antibiotic 10381b complex was tested for growth promotion and/or feed conversion indications in the broiler chick. The mean growth index (gain/3 + feed conversion) of the antibiotics 10381b was greater than three and significantly (P<=0.20) greater than zero. Thus, by the criteria for the primary screen, antibiotics 10381b passed. (The mean growth index measures the improvement in growth over controls (chicks given feed without additin of drug).) |

TABLE 11

ANTIBACTERIAL IN VITRO TESTING OF
ANTIBIOTIC 10381b$_2$ (MINIMUM INHIBITORY CONCENTRATION
(MIC)) (MIC MEDIUM: MHA)

| Organism | Culture # | MIC (mcg/ml) |
|---|---|---|
| *Enterobacter cloacae* | UC 9381 | >256 |
| *Enterobacter cloacae* | UC 9382 | 256 |
| *Klebsiella oxytoca* | UC 9383 | >256 |
| *Klebsiella oxytoca* | UC 9384 | 256 |
| *Escherichia coli* | UC 9379 | 256 |
| *Escherichia coli* | UC 9380 | 256 |
| *Staphylococcus aureus* | UC 6675 | 1 |
| *Staphylococcus aureus* | UC 3665 | 1 |
| *Staphylococcus aureus* | UC 6685 | 1 |
| *Streptococcus pyogenes* | UC 152 | 0.125 |
| *Streptococcus pneumoniae* | UC 41 | 0.125 |
| *Streptococcus faecalis* | UC 694 | 0.25 |
| *Escherichia coli* | UC 311 | >256 |
| *Klebsiella pneumoniae* | UC 58 | 128 |
| *Pseudomonas aeruginosa* | UC 9191 | >256 |
| *Pseudomonas aeruginosa* | UC 6432 | >256 |
| *Serratia marcescens* | UC 6888 | >256 |
| *Citrobacter freundii* | UC 3507 | >256 |
| *Proteus vulgaris* | UC 30264 | 256 |

TABLE 12

CHARACTERIZATION OF ANTIBIOTIC 10381a$_1$
HYDROCHLORIDE

1. Appearance: Colorless amorphous material.
2. Melting point: ca 120° C. with decomposition.
3. $[\alpha]^{25}_D$, +40° (C., 0.897, water).
4. UV: $\lambda$max = 271; $\alpha$ = 14.64; $\epsilon$ = 7950.
5. IR Band Tabulation:

| Band Frequency | Intensity | Type | Band Frequency | Intensity | Type |
|---|---|---|---|---|---|
| 3343.5 | 18 | BRD | 2019.4 | 86 | BRD |
| 3200.8 | 18 | BRD | 1727.2 | 25 | AVG |
| 3066.8 | 24 | BRD | 1655.8 | 5 | BRD |
| 2948.1 | 0 | BRD M | 1632.7 | 9 | SH |
| 2909.6 | 0 | BRD M | 1537.2 | 26 | BRD |
| 2868.1 | 1 | SH M | 1493.8 | 33 | AVG |
| 2853.6 | 0 | AVG M | 1462.0 | 12 | AVG M |
| 2733.1 | 52 | SH M | 1398.3 | 42 | BRD |
| 2674.2 | 57 | SH M | 1378.1 | 21 | SHP M |
| 1340.5 | 52 | SH | 897.8 | 72 | BRD |
| 1296.1 | 49 | SH | 865.0 | 67 | AVG |
| 1271.0 | 42 | AVG | 826.4 | 59 | AVG |
| 1242.1 | 40 | AVG | 804.3 | 60 | SH |
| 1197.7 | 52 | AVG | 779.2 | 51 | AVG |
| 1120.6 | 48 | AVG | 763.8 | 56 | SH |
| 1074.3 | 39 | AVG | 721.3 | 45 | AVG M |
| 965.3 | 68 | BRD | 649.0 | 44 | SH |

Band Frequency: Band frequencies in wavenumbers (CM$^{-1}$)
Intensity: Intensity in percent transmittance (% T)
Data Type in Local Peak Region: BRD = Broad; AVG = Average; SHP = Sharp; SH = Shoulder.
M: Possible interference from mineral oil.

TABLE 13

CHARACTERIZATION OF ANTIBIOTIC 10381a$_1$
METHYL ESTER

1. Appearance: Colorless amorphous material.
2. Melting point: ca 110° C. (decomposition).
3. $[\alpha]^{25}_D$, +15° (C., 1.03, water).
4. UV: $\lambda$max = 268; a = 13.21; $\epsilon$ = 5950.
5. IR Band Tabulation

IR BAND TABULATION OF ANTIBIOTIC 1038A$_1$
METHYL ESTER HYDROCHLORIDE

| Band Frequency | Intensity | Type | Band Frequency | Intensity | Type |
|---|---|---|---|---|---|
| 3333.9 | 21 | BRD | 1735.9 | 11 | AVG |
| 3194.1 | 18 | BRD | 1679.9 | 4 | AVG |
| 3047.5 | 20 | BRD | 1659.7 | 8 | SH |
| 2960.7 | 0 | BRD M | 1631.7 | 13 | AVG |
| 2853.6 | 0 | AVG M | 1539.1 | 29 | AVG |
| 2733.1 | 47 | SH M | 1461.0 | 11 | AVG M |
| 2671.4 | 55 | SH M | 1377.1 | 23 | SHP M |
| 2639.5 | 58 | SH | 1366.5 | 37 | AVG |
| 2007.8 | 91 | BRD | 1312.5 | 56 | SH |
| 1267.2 | 32 | AVG | 936.4 | 76 | SH |
| 1239.2 | 35 | AVG | 894.0 | 77 | BRD |
| 1215.1 | 46 | AVG | 866.0 | 70 | AVG |
| 1195.8 | 48 | AVG | 824.5 | 61 | AVG |
| 1122.5 | 47 | AVG | 779.2 | 57 | AVG |
| 1082.0 | 45 | AVG | 764.7 | 60 | AVG |
| 1013.5 | 66 | AVG | 721.3 | 49 | AVG M |
| 965.3 | 74 | BRD | 647.1 | 45 | BRD |

Band Frequency: Band frequencies in wavenumbers (CM$^{-1}$)
Intensity: Intensity in percent transmittance (% T)
Data Type in Local Peak Region: BRD = Broad; AVG = Average; SHP = Sharp; SH = Shoulder.
M: Possible interference from mineral oil.

TABLE 14

Mean Improvement in Gain and Feed Conversions and Mean Growth Indexes by Trials

| | | Mean Improvement In | | |
|---|---|---|---|---|
| Trial | Treatment | ADG | F/G | Growth Index |
| 1 | 10,381b | 21.97 | 7.88 | 29.85 |
| 2 | 10,381b | 14.48 | 8.11 | 22.59 |
| 3 | 10,381b | 19.26 | 4.37 | 23.63 |
| 4 | 10,381b | 29.21 | 12.78 | 41.99 |
| OVERALL | 10,381b | 21.23 | 8.29 | 29.52 |

TABLE 15

Statistical Parameters and t-Test

| 10,381 b | 0–21 Days |
|---|---|
| Mean Growth Index | 29.52 |
| t | 6.62 |
| Prob. Mean is < = 0.0 | 0.0004 |
| Variance Components: | |
| Trials | −12.435 |
| Blocks (trial) | 734.783 |
| Total | 734.783 |

FORMULA CHART

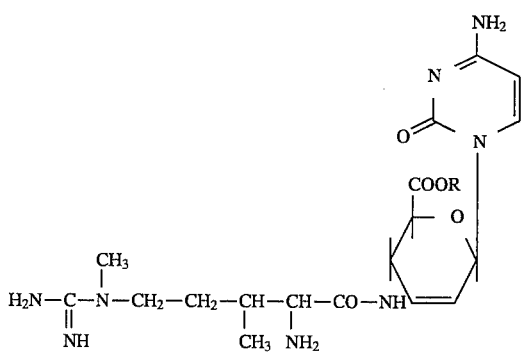

We claim:
1. A method for promoting growth in chickens which comprises: administering to the chickens an amount of antibiotics 10381b effective to promote growth, by adding the antibiotics to the feed of the chickens in an amount from about 0.5 to about 11 mg per kilogram of the chickens' feed.

2. A method for promoting growth in swine which comprises: administering to the swine an amount of antibiotics 10381b effective to promote growth, by adding the antibiotics to the feed of the swine in an amount from about 10 to about 55 mg per kilogram of the swine's feed.

* * * * *